(12) United States Patent
Hughes

(10) Patent No.: US 10,433,529 B2
(45) Date of Patent: Oct. 8, 2019

(54) WORM CULTURE SYSTEMS

(75) Inventor: Kenneth D. Hughes, Alpharetta, GA (US)

(73) Assignee: Kenneth D. Hughes, Alpharetta, GA (US)

( * ) Notice: Subject to any disclaimer, the term of this patent is extended or adjusted under 35 U.S.C. 154(b) by 876 days.

(21) Appl. No.: 13/031,573

(22) Filed: Feb. 21, 2011

(65) Prior Publication Data

US 2012/0214223 A1   Aug. 23, 2012

(51) Int. Cl.
  *C05F 17/02* (2006.01)
  *A01K 67/033* (2006.01)
  *C05F 17/00* (2006.01)

(52) U.S. Cl.
  CPC ...... *A01K 67/0332* (2013.01); *C05F 17/0009* (2013.01); *C05F 17/0205* (2013.01); *C05F 17/0211* (2013.01); *Y02P 20/145* (2015.11); *Y02W 30/43* (2015.05)

(58) Field of Classification Search
  CPC ........ C05F 9/02; C05F 17/0009; C05F 17/02; C05F 17/0205; C05F 17/0211; C05F 17/0247; C05F 17/0257; A01K 67/033; A01K 67/0332; B65D 88/16; B65D 88/1612; B65D 88/1643; B65D 88/1668; B65D 88/1681; B65D 88/1687; B65D 88/1693

See application file for complete search history.

(56) References Cited

U.S. PATENT DOCUMENTS

| | | | | |
|---|---|---|---|---|
| 4,759,473 A | * | 7/1988 | Derby | B65D 88/1618 222/105 |
| 4,901,885 A | * | 2/1990 | Boots | B65D 88/1625 220/646 |
| 4,913,321 A | * | 4/1990 | Abboud | B65D 88/72 222/105 |
| 5,108,196 A | * | 4/1992 | Hughes | 383/17 |
| 5,538,860 A | * | 7/1996 | Castelli | C05F 17/00 220/908 |

FOREIGN PATENT DOCUMENTS

WO    WO 0032540 A1 *  6/2000

* cited by examiner

*Primary Examiner* — William H. Beisner
(74) *Attorney, Agent, or Firm* — F. Brent Nix, Esq.; Johnson, Marcou & Isaacs, LLC

(57) ABSTRACT

Devices and methods are disclosed for the containment and culture of worms, and the preparation of composts, vermicomposts, and castings from organic and inorganic wastes.

17 Claims, 5 Drawing Sheets

WORM CULTURE SYSTEMS

FIELD OF THE INVENTION

The herein disclosed invention is directed at devices and methods for their use for the housing and culture of worms and insect larvae, the preparation of compost, vermicompost, and castings, and the processing of these materials. Devices and methods provide great economy and are beneficial to many Industries including waste management, environmental remediation, agriculture, horticulture, and outdoor recreation.

BACKGROUND OF THE INVENTION

The transformation of organic and inorganic wastes into beneficial materials by earthworms and insect larvae have been known for thousands of years. Currently, these organisms are receiving global interest for assisting in the managing of modern organic waste streams.

The US EPA estimates that approximately 600 million tons of compostable organic waste from residential, commercial, and industrial sources was land-filled, land-spread, or incinerated, in 2009. Typical US households discard 500 lbs of food scrap yearly, while retail food outlets discard more than 100 pounds of food scrap daily. Land-filling, land-spreading, and incinerating these wastes often degrades water and air systems, generating green house gases and sequestering significant amounts of plant nutrients that could be recycled and reused for commercial and residential agriculture and gardening.

The application of worms and insect larvae in controlled and sophisticated manners holds tremendous promise in resolving these waste management problems. Composts and metabolic excretions generated by earthworms, often referred to as vermicompost and castings, respectively, are widely recognized for their value as fertilizers and soil amendments, as well as their ability to improve plant health, growth, and yields. Worms and insect larvae are well recognized as a food source for both humans and animals, and still remain an important component of outdoor recreational activities.

DESCRIPTION OF RELATED ART

The use of earthworms and insects for the transformation of wastes is well established. Exemplary wastes include animal wastes, agriculture, horticulture, and landscape wastes, municipal wastes that contains food scraps, paper, and organic household materials, and industrial wastes that contain cellulose, minerals, and other natural materials.

The use of worms to transform waste has been demonstrated on both small and large scales. However, as the EPA numbers provided vide supra indicate, there has been limited application of this biotechnology in the field of waste management. Reasons for this limited implementation include lack of convenience, cost-effectiveness, and the knowledge required to apply worm technologies in locations where wastes are generated.

Current devices, equipment, and methods for vermicomposting and composting on commercial, farm, and residential scale have been recently reviewed by Edwards, Arancon, and Sherman in *Vermiculture Technology: Earthworms, Organic Wastes, and Environmental Management*, CRC Press, 2010. As this review and others indicate there is still significant need for improvement in both methods and devices.

At the residential level, the use of small containers containing air holes for housing worms and performing vermiculture and vermicomposting have been described. Exemplary designs include U.S. Pat. Nos. 332,163; 6,576,462; 4,108,609; 3,961,603, 3,654,903; US 2010/0273251 (application); US 2003/0059931 (application); and WO/2000/053543. Commercial products based on these designs are now generally available. Similar size devices and designs have also been described for residential composting efforts. Exemplary designs include U.S. Pat. No. 5,894,780, and WO/2006/042166. While each of these devices are designed to provide operational convenience for consumers and home owners for transforming small amounts of wastes, they are difficult to use for cross purposes and typically produce an inferior vermicompost and castings product compared to large scale production systems.

As example, U.S. Pat. No. 3,961,603 describes a ground based vermiculture system prepared with stackable trays. Trays can be repositioned when needed to provide continuous operation. This type of design is not well suited for composting. WO/2000/053543 describes a small elevated vermicomposting system that not only suffers from an inability to be efficiently positioned or operated on the ground, but is difficult to use for any other purpose and must be placed in an optimum environment for good results. U.S. Pat. No. 5,894,780 and WO/2006/042166 also incorporate low cost materials, however, they cannot be used with mobile animals such as worms due to direct ground contact, and imprecise control over container openings. Both of these designs also suffer from operational difficulties which include controlling device shape, size, and position when loading and unloading materials and similar device instabilities that occur during waste transformation.

In general, these exemplary and similar small scale designs suffer from numerous physical, economical, and operational limitations that restrict scale-up for transforming large continuous waste streams that require precise control of processing conditions including temperature, moisture, lighting, and oxygenation, as well as efficient material handling including loading of wastes and feedstocks and unloading of finished products.

Many large scale worm propagation, composting, and vermicomposting operations still utilize traditional methods for handling and manipulating large volumes of organic materials. The use of windrows and piles (heaps) are common and can be operated outdoors or indoors. Piles are often organized in bunkers with two or more solid structures serving as walls and cement floors. Windrows and small piles while convenient and simple to operate are space inefficient and difficult to control with respect to environmental parameters. Leachate and nutrient run-off associated with large and small piles maintained outdoors is a growing problem. Solutions to these problems have included moving piles indoors or under structures, placing breathable fabrics over top of the piles, constructing complex drainage systems, and using large ground based containers. Attempts to conduct composting in low cost containers as described in U.S. Pat. Nos. 5,538,860 and 5,632,798 has proven difficult due to the lack of structure of the container and inefficiencies in material loading and unloading operations. As a result, most in-vessel composting operations use rotary drums, and rectangular vessels sized similar to transport containers. Additionally, while these design strategies may be functional for thermophyllic or hot-composting of organic materials they present significant difficulties when working with worms and insects due to organism mobility, and the need to separate and isolate transformed materials, unprocessed feedstocks (waste), and animals.

The use of ground based industrial sized containers or stacked bins for vermicomposting and vermiculture has been investigated and reviewed by Edwards, Arancon, and Sherman in *Vermiculture Technology: Earthworms, Organic Wastes, and Environmental Management*, CRC Press, 2010. In general, bins, crates and small containers are not commercially viable due to the lack of environmental controls including temperature, moisture, and oxygen, labor intensive material handling operations, and difficulties in separating finished products from starting wastes and animals.

Limitations to ground based vermiculture and vermicomposting methods have been addressed by implementing large volume elevated vessels that facilitate continuous loading of wastes and continuous collection of vermicompost and castings. These large vessels typically have two rigid solid side walls, an open top for waste material input, and a mesh floor for discharging vermicompost and castings. Elevating containers above ground creates a void space under the container that enables a "flow-through" system to be created, where feedstocks and organic wastes are placed into the top of the container and vermicompost and castings are collected from under the container. The worms, in theory, continually work their way to the surface of the container and are therefore not lost through the mesh floor. In practice, heating elements, lighting and increased air flow under devices is used to reduce animal losses. Elevated vessels using flow-through methods can provide higher quality vermicompost and casting products than windrows and piles as there is better separation between starting waste materials and final products.

Exemplary elevated vermicomposting systems are described in U.S. Pat. Nos. 7,422,894; 6,223,687; US 2008/0251021 (application); U.S. Pat. No. 7,141,169; US 2006/0131229 (application); U.S. Pat. No. 6,776,568, and US 2002/0144658 (application). These systems provide high waste throughputs and generate high quality final products but are expensive and time-consuming to build, complex to operate, and not portable. Efficient operations require a continuous and chemically and physically consistent waste stream. The open tops and mesh bottoms of these large vessels provide operational efficiency but the need for additional lighting, temperature, or air movement to confine worms, increases energy requirements. In practice, vessel coverings such as tarps are also needed for additional heat and moisture control. When elevated devices with large surface areas are installed outdoors or without overhead cover, system control is much more difficult.

As a result, there is a need for new vermicomposting, composting, vermiculture, and worm propagation devices and methods that provide rapid efficient transformation rates for wastes and feedstocks, are low-cost and simple to construct and disassemble, and that operate at ground level or elevated above ground. There is a need for devices that are easily portable while containing animals, and that can generate high quality vermicompost, compost, and castings that are easily separated from animals and starting feedstocks (wastes). Additionally, there is an immediate need for devices and methods that can efficiently and cost effectively meet the on-site needs of medium and large sized waste streams, provide efficient transportation and storage for vermicompost, compost, and castings, and provide a means for manipulating vermicompost, compost, and castings at the site of their final application.

SUMMARY OF THE INVENTION

The instant invention involves devices and methods for their use for the housing, culture, and propagation of worms and insect larvae, and the production of vermicompost, compost, and castings. Exemplary devices are prepared with flexible, high-strength, light-weight, and breathable thin polymer films for all surfaces, and operated in a flow-through manner with waste materials and feedstocks placed into the top of devices and vermicompost, compost, and castings removed from the bottom of devices. Exemplary devices of the invention comprise lids and floors with integrated chutes, spouts, or meshes for efficient material handling. Preferred devices of the invention comprise simple internal rigid or semi-rigid support structures that maintain the internal volume space when used directly on ground level, elevated above ground, and when the internal volume is partially or fully filled. Preferred devices comprise an integrated resealable lid that aids in controlling moisture, lighting, and air flow. Devices support batch, continuous, and semi-continuous operation.

Devices of the invention are modular, light-weight, stackable, and transportable, using lifts, hoists, and related equipment. Devices of the invention can be efficiently transported using standard road, rail, and water methods. Devices are suitable for operation indoors as well as outdoors and moving between locations.

The utility of the instant invention is far reaching and provides significant benefits that have not been previously described in the fields of vermiculture, composting, vermicomposting, or waste management on any scale. It is therefore an object of this invention to provide light-weight, operations efficient, and portable enclosed devices and methods for their use to culture and propagate worms and to produce and collect the byproducts of their metabolism, including vermicomposts and castings. It is also an object of this invention to provide lightweight, efficient, and portable enclosed devices and methods for their use to culture and propagate insects and to produce and collect the byproducts of their metabolism.

Objects of this invention include, treating and transforming organic and inorganic wastes into useful materials with application in agriculture, horticulture, and landscaping, and providing devices for research and testing of soils and agricultural products that could lead to soil toxicity. It is an object of this invention to provide devices suitable for both producing, storing, and transporting vermicomposts, composts, and worm castings as well as manipulating and processing these materials for application.

Objects of this invention include preparing composted waste materials to be used as feedstocks for vermiculture, vermicomposting, and insect larvae culture; exposing wastes and feedstocks to a process of thermophyllic and mesophyllic temperature treatment in order to prepare materials for vermiculture, vermicomposting, and insect larvae culture, and exposing feedstocks to a process of thermophyllic temperature treatment where temperatures are sufficient to reduce pathogens and weed seeds. Objects of the invention further include producing composts, vermicomposts, castings, and worm and insect biomass in a uniform method with lower labor demands, better control of culture conditions, and more predictable product quality, and providing high quality worm and insect metabolism byproducts that are easily separated from starting waste materials and feedstocks.

Objects of this invention include providing devices for use in mobile waste stream management operations, and allowing vermiculture, vermicomposting, and insect larvae propagation operations to be conducted in residential and urban areas with high efficiency, and in a manner that satisfies regulatory requirements.

BRIEF SUMMARY OF FIGURES

The accompanying drawings are included to provide a further understanding of the invention, and are incorporated in and constitute a part of this specification. The drawings are not necessarily to scale, and sizes of various elements may be distorted for clarity. The drawings illustrate one or more embodiment(s) of the invention, and together with the description serve to explain the principles and operation of the invention.

DETAILED DISCUSSION

Figure 1:
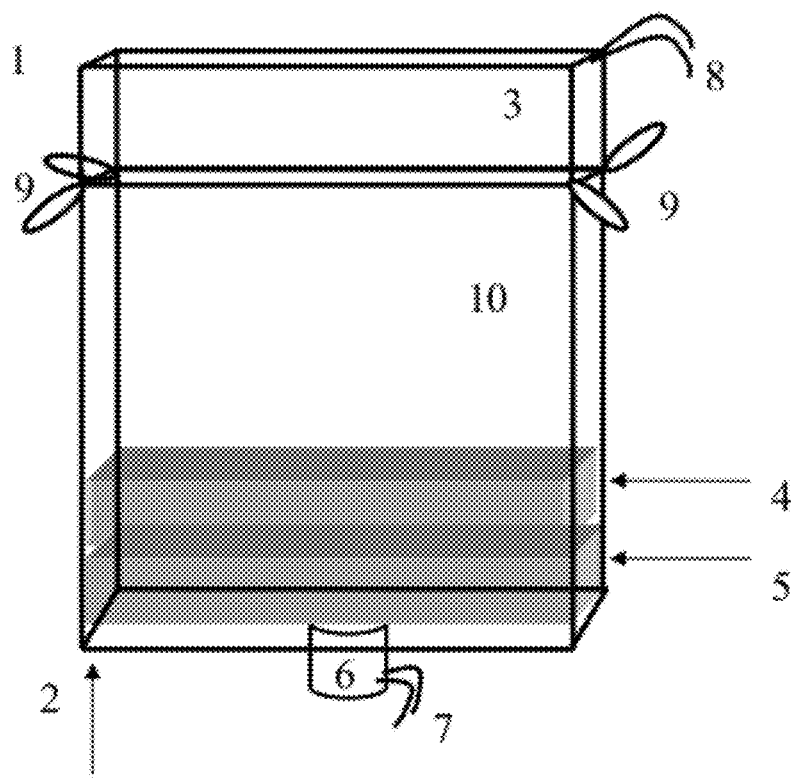
FIG. 1, a front view, illustrates one embodiment of the invention, a rectangular device made from high strength, woven, flexible, and breathable thin polymer films, incorporating a single internal volume space, a resealable lid, discharge chute, and integrated handles for elevation and transport.

The disclosed invention involves the care, feeding, culture, propagation, and production of worms, insect larvae, and microorganisms inside light-weight portable devices, as well as the production of worm, insect, and microorganism metabolic byproducts including compost, vermicompost, and castings. The disclosed invention also involves the management and transformation of organic and inorganic wastes into beneficial products useful in agriculture, horticulture, and gardening. There are many different organic and inorganic wastes that may be subject to transformation with devices of the invention and they include animal wastes of all types, agriculture, horticulture, and landscape wastes, municipal wastes that contains food scraps, paper, and organic household materials, and industrial wastes that contain organics and minerals, as well as cellulose and other natural polymers.

Exemplary devices of the invention are prepared with high strength, flexible, and breathable thin polymer film materials in a manner that defines an internal volume space. Preferred devices use breathable films for all surfaces. While many device geometries are possible cylinders, barrels, squares, and rectangles are preferred. Exemplary devices utilize rigid or semi-rigid, hollow or solid support structures or frames for maintaining device shape while allowing maximum gas exchange between device internal volume space and the external atmosphere. Exemplary devices combine high strength polymer film materials and rigid or semi-rigid support structures by sewing, integrated weaving, thermally sealing, adhesives, or a combination thereof.

Exemplary devices are operated in a flow through manner by placing organic and inorganic waste and feedstock materials into the top of devices and removing finished materials including compost, vermicompost, and castings from the bottom of devices. Exemplary devices can be operated on the ground, elevated above ground, or a combination thereof. Additionally, exemplary devices are modular, conveniently positioned, and easily transportable while the internal volume space is filled completely, or partially filled with animals, composts, vermicomposts, castings, or a combination thereof.

Preferred devices provide control of environmental conditions inside devices including temperature, humidity, lighting, moisture, and oxygen levels. Preferred devices facilitate the storage, transport, and manipulation of animals, composts, vermicomposts, and castings in the same device as their production. Further, preferred devices allow composts, vermicomposts, and castings to be processed for application in agriculture, horticulture, and landscaping.

Preferred devices can be fully enclosed comprising top and bottom films that serve as lids and floors which allow repeated opening, closing, and temporary sealing. Exemplary devices facilitate transport and elevation using integrated handles, loops, straps and sleeves, with preferred devices allowing rotation of the device in three dimensions. Preferred devices include thin polymer film or molded loading and unloading design elements such as ports, chutes, and spouts.

The disclosed invention has broad industrial applicability as it involves the propagation and production of worms, insect larvae, and microorganisms that can transform a wide range of organic and inorganic wastes into beneficial products useful in agriculture, horticulture, and gardening. Organic and inorganic wastes that are suitable for transformation with devices of the invention include animal wastes of all types, agriculture, horticulture, and landscape wastes, municipal wastes that contains food scraps, paper, and organic household materials, and broad range of industrial wastes that contain organic materials, inorganic materials, minerals, and complex mixtures thereof. Devices of the invention provide cost effective transformation of wastes through vermicomposting, production of castings, thermophyllic composting, and mesophyllic composting.

The beneficial aspects of composts have been frequently described and are widely understood. Unfortunately, the beneficial aspects of vermicomposts and worm castings are less well understood due to limited study and infrequent application. In addressing this problem, devices of the invention allow low-cost and convenient application of worms and insect larvae to the management of compostable waste streams. Worm castings, in particular, have demonstrated promise as a superior plant nutritional source, useful for soil revitalization, and for the control of plant diseases and pests. It is highly anticipated that these materials can displace significant amounts of synthetic fertilizers now in use and that are causing environmental damage from run-off, displace and eliminate the use of many pesticides and fungicides that require frequent application, and provide a basis for restoring soil vitality in both residential and commercial landscaping applications.

Devices of the invention are light-weight, modular, portable and allow high efficiency composting, vermicomposting, and vermiculture processes to be implemented and established on a scale suitable for handling both medium and large scale continuous volumes of compostable wastes. Devices of the invention are quick to setup, quick to disassemble, and stable in the presence of a wide range of wastes, and can be used indoors or outdoors. Devices are useful for testing and researching soils, soil toxicity, and ascertaining the impact of agricultural products on soils and soil organisms.

General embodiments include use of devices that are made with thin, flexible, breathable polymer films, which comprise tops or lids and bottoms or floors and define an enclosed volume space. General embodiments include devices in the shape of squares, rectangles, barrels, and cylinders, and devices that comprise integrated rigid or semi-rigid support structures or frames that allow devices to maintain the internal volume space when supported on a surface, elevated, or hanging. General embodiments include devices that comprise integrated rigid or semi-rigid support structures or frames that allow devices to maintain a full internal volume space when partially and fully filled.

General embodiments include devices that can be rapidly loaded and unloaded using lids and floors that fully open or by using lids and floors with integrated chutes, spouts, or specialized apertures. Rapid loading and unloading allows efficient batch processing as well as allowing device contents to be frequently sorted, mixed, separated, sieved, treated, and harvested. General embodiments include the use of sealing ties, straps, clips, and fasteners that allow opening, closing, and resealing of device floors and lids.

General embodiments include devices with open lids, open floors, or combinations thereof, for the continuous introduction of feedstocks and wastes into the top of devices, and the continuous removal of composts, vermicomposts, castings, and animals, and combinations thereof from the bottom of devices. General embodiments include devices with lids and floor films that contain design elements including chutes, spouts, and ports for continuously introducing feedstocks and wastes into the top of devices, and continuously or semi-continuously removing composts, vermicomposts, castings, and animals, and combinations thereof, from the bottom of devices. General embodiments include devices that function with common aeration, heating, and lighting equipment as well as simple light blocking and insulating materials.

General embodiments include the printing and marking of devices in a manner that enhances the marketing and aesthetics of using the devices as well as in a manner that increases the operational utility and convenience of using and manipulating devices of the invention.

General embodiments include devices that are free standing, supported above ground using legs or ground level supports, and supported above ground using hanging structures and elevated structures. General embodiments include devices that can be rotated in three-dimensions using integrated handles, straps, sleeves, and loops. General embodiments include the use of groupings, stacks and arrays of devices where devices are in close contact with one another for storage and can be rotated through different locations within groupings, stacks or arrays to control temperature exposure and other environmental conditions. General embodiments also include the organization of devices in groups, stacks, and arrays in a manner that allows the output or discharge of one device to serve as the input or feedstock for a second device.

General embodiments include devices that can be used in the preparation of compost, vermicompost, and castings, the preparation of extracts, teas, liquid suspensions, and combinations thereof from these materials, and the housing, culture, and propagation of large quantities of animal biomass. General embodiments include devices which are inexpensive and minimize impact on the environment when needing disposal, through the minimization of raw materials and use of recyclable materials. General embodiments include devices that are made on demand from rolled film stocks.

In general, a device is an enclosed volume space or container formed with thin flexible polymer films sealed around their edge. Preferred polymer films are breathable allowing gas exchange between the internal volume space of the device and the external atmosphere, but are not waterproof, allowing bulk water to pass. These characteristics allow organisms requiring oxygen to survive inside the device when fully enclosed and bulk water to be discharged from inside the device. Preferred materials inhibit bulk water from entering the device, but are not waterproof.

Exemplary devices of the invention have square, rectangular, barrel, or cylinder shapes, and flat or conical bottoms or floors that allow device shape to be maintained when supported on the ground, hanging from supports, and when partially or fully filled. Preferred device shapes are square and rectangular, and include tops or integrated lids that allow complete enclosure of devices. These geometries and characteristics facilitate automated or manual loading and unloading of wastes, feedstocks, finished products and organisms, using standard equipment including hoppers, chutes, hoists, lifts, conveyors and buckets.

Preferred device dimensions include lengths between 12 inches and 48 inches, widths between 12 inches and 48 inches, and heights between 12 inches and 96 inches. Preferred device dimensions include those that provide internal volume spaces between 0.5 cubic yards and 5 cubic yards. More preferred device dimensions provide internal volume spaces between 0.5 cubic yards and 2 cubic yards. Internal volume spaces of approximately one cubic yard facilitate temperature and moisture stability and thus stability in worm and insect culture. Further, internal volume spaces of approximately one cubic yard allow wastes and feedstocks to experience thermophyllic composting stages of 55° C. or greater for 48 hours or longer, and meet regulatory requirements for public use.

Preferred device internal volume spaces are suitable for meeting the waste disposal needs of several residences, retail food and beverage outlets, and locations that generate approximately 100 lbs of compostable waste per day. When waste volumes exceed this amount several devices of similar size can be employed with equal efficiency.

Preferred materials for device fabrication include strong, thin flexible polymer films which are breathable, and liquid permeable. Breathable films allow maximum gas exchange, including oxygen, carbon dioxide, and water vapor, between the external device atmosphere and a device's internal volume space. Composting, vermicomposting, and vermiculture are aerobic processes requiring continuous access to oxygen and removal of carbon dioxide. Liquid permeable films also allow moisture in the enclosed device volume space to be controlled and manipulated. Preferred thin polymer films allow bulk water to quickly pass out of devices but allow elevated humidity environments to be generated and maintained inside devices. Of equal importance is the bulk water blocking characteristics of preferred films which block precipitation and bulk water from entering devices. Preferred films and polymers used to generate films do not absorb significant quantities of water which can impact material porosity and reduce breathability. Preferred devices utilize flexible, breathable thin polymer films for all surfaces.

Thin polymer films may be manufactured using synthetic polymers, natural polymers, or a combination thereof. Thin polymer films useful for devices can be woven, non-woven, knitted and comprise complex laminates Preferred thin polymer films are synthetic, woven, and do not use coatings or laminations that block gas exchange. Woven films that maximize gas exchange while retaining mobile organisms such as worms, flying insects, and insect larvae are preferred. When nonwoven films are used it is desirable to maximize porosity to improve gas exchange. Those expert in the field will understand the pore density required to maximize gas exchange while maintaining structural integrity. Likewise, experts in the field will understand how to laminate and provide coatings to woven and nonwoven polymer films that allow gas exchange to occur while retaining structural integrity, and providing device protection from radiation, and other environmental conditions.

Exemplary devices are prepared with more than one thin polymer film. Preferred devices incorporate four panels, two panels, tubular formed films, and u-shaped films. The thin polymer films are sealed together by sewing, thermal sealing, application of adhesives and a combination thereof. When devices are sewed they can include yarns, felts, and other materials in seams to reduce the leakage of solid materials. Preferred devices have stitched and reinforced seams that provide strength and maintain shape. Exemplary stitching methods includes chain and overlock.

Preferred devices are prepared with integrated handles, support straps, loops, sleeves, and combinations thereof for use in lifting, positioning, and transport of devices, as well as aiding in the retention of device shape. These device elements can be integrated by sewing, thermal sealing, application of adhesives and a combination thereof.

Preferred thin polymer films have material weights between 1 and 20 ounces and more preferred between 3 and 8 ounces. Exemplary weave patterns include plain square, plain reverse dutch weave, twill weave, and satin weave. Exemplary devices can comprise different weight materials for lids, floors, and side panels. Those knowledgeable in the field will understand the limitations associated with material weight and manual or automated closure mechanisms for device lids and floors. Additionally, support straps, handles and lifting elements can utilize different weight materials than the device walls.

Preferred films are opaque, however devices can include one or more transparent films for viewing device contents and for educational purposes.

Preferred polymers for use in preparing thin polymer films include polypropylene, polyethylene, polyamide, PEEK, PTFE, E-CTFE, PVDF, tyvek, gore-tex as well as building and landfill construction membranes.

Exemplary materials that may also be used to prepare devices of the invention include, thermoplastic elastomers such as polystyrene-dienes, polyurethanes, copolyester-ethers; PVDC, OPP, EVOH, nylon, EVA, EAA, EMA, LLDPE, VLDPE, ULDPE, ionomers, metallocenes, PP, PCTFE, ECTFE, PET/PETG, as well as laminates and blends of materials including Bynel, Crystar, Dartek, Elvaloy, Delrin, polyethers of formaldehyde/ethylenoxide, polyethylene, polystyrenes, polyvinyl chlorides, ionomers, polyethylene terephthalates, polyvinyl acetates, polycarbonates, polyamides, polyvinyl alcohols, polyvinylidene chlorides, ethylene acrylate copolymers including butyl-, ethyl- and methyl-acrylates (EBAs, EEAs and EMAs), nylons, celluloses, polypropylenes, polybutadienes and polyisoprenes, polyvinylchlorides, propanediols, fluorinated polymers including Teflon, polyesters, Tyvek, and tyvek-type materials, Gore-Tex and Gore-Tex type materials, foil based films, clear foil laminations, and metallized polyester-polyethylene laminations. Many of the listed materials are used commercially in the food, chemical, pharmaceutical, consumer apparel, and outdoor gear, and construction industries.

Thin film material may include woven metallic elements including fibers, strands, bands, ropes, and cables which allow devices to be heated, and electrically grounded for outside use. Additionally, these elements can be used to control the movements and locations of animals inside a device, as well as to provide additional support for maintaining the internal volume space. Preferred metallic elements are conductive and inhibit oxidation.

Those experienced in the field will understand that material thickness and weight is an important variable in device construction and that varying degrees of flexibility, handling, and breathability are associated with each material type. Additionally, those knowledgeable in the art will understand the incompatibilities that exist between specific materials types and the chemical, physical, and biological nature of device contents, as well as the environmental conditions that are suitable for devices prepared with those materials. Experts in the field will also understand how to sanitize and sterilizer the different types of materials that are suitable for construction of devices of the invention.

Preferred devices of the invention include integrated internal support structures that provide significant utility including, maintaining internal volume space when devices are supported on ground level supports, hanging above ground, when fully or partially filled, when devices are rotated in three dimensions, and when devices are transported. Integrated internal support structures can also assist in controlling environmental conditions inside devices, delivering and removing materials, providing compartments or zones for isolating organisms, processes, materials, and combinations thereof.

Integrated device supports are important for operations including waste transformation efficiency, and material handling. Without support structures devices prepared with flexible films change dimensions when devices are loaded with wastes and feedstocks, when finished products are discharged from devices, when wastes and feedstocks undergo transformation, settling, and changes in density, when device elevation is changed and when devices are moved and transported. These dimensional changes impact the ability to reversibly seal and unseal devices, alter surface areas which are important for controlling loading and unloading materials, controlling internal environmental conditions, and optimizing the spatial locations of organisms participating in the transformation. Dimensional changes can also impact the heterogeneity of device contents with undesired mixing.

Integrated internal support structures are prepared with rigid or semi-rigid metal, wood, or plastic materials that allow the thin polymer films of the invention to remain taut and maintain the shape and internal volume space of the device. Exemplary internal structures for devices of the invention can be temporarily placed or permanently fixed into position. Exemplary methods of positioning and securing internal structures inside devices include sewing directly to films, use of dedicated sleeves, weaving into films, heat sealing, adhesives, and combinations thereof.

Internal structural supports of devices can also be used to manipulate and control environmental conditions within the internal volume space working synergistically with the thin breathable polymer films. Internal support structures prepared with hollow and perforated conduits and pipes can provide aeration, temperature, and moisture control and provide a means for loading devices with wastes, feedstocks, adjuvants, culturing agents, and organisms, as well as provide a means for discharging finished products, animals and moisture from devices. Hollow supports can also provide protected locations for organisms.

Internal support structures can provide both passive atmosphere exchange between external atmospheres and internal volume spaces through fixed and variable openings and pressurized gas exchange when structures are attached to external pressure or vacuum pumps, fans, compressors and related gas transfer equipment. Likewise, humidity, and temperature control can be implemented in passive or pressurized arrangements by providing conduits to the external atmosphere or using standard humidification equipment. Moisture can be directed into devices through piping and conduits and distributed throughout using common methods including nozzles, perforated and porous materials, and drip systems. Temperature inside devices can be further controlled using a combination of air flow, moisture, and humidity characteristics. Manual and automated equipment are widely available for monitoring and controlling environmental parameters inside devices of the invention. Experts in the field will understand how to incorporate sensors and monitoring equipment into devices for adjusting environmental parameters and meeting the process requirements for operations including composting vermicomposting, and the culture of worms and insects.

Exemplary internal device structures are prepared with wood, wood composites, metal, metal composites, nonmental composites, plastics, and combinations thereof. Preferred materials include plastics, metals, and bamboo like natural materials suitable for water and solution contact. Preferred materials are light weight but strong and include perforated or slotted pvc pipe. Porous and perforated materials can comprise barrier materials using coatings, material wraps, and meshes to control access by organisms involved in composting, vermiculture, and vermicomposting operations. There are many types of commercially available solid rod and hollow piping and tubing materials that are suitable for use inside devices. Experts in the field will understand the costs and suitability of each material type for use in composting, vermicomposting, and culturing worms and insects.

Internal support structures can also include rigid or semirigid cable, wires, bands, and ropes. These materials can be flat or round and affixed on the inside surface of the thin polymer films or woven into the thin polymer films. These materials can have great utility by providing flexibility to the sides of devices but high compression strength between the top and bottom of devices. Experts in the field will understand the required length and diameter of materials required to obtain the desired result.

Internal support structures can also include rigid or semirigid meshes. Mesh materials may have a wide range of opening sizes. A preferred location for mesh structures is the bottom or floor of devices where the mesh serves to support the device shape and internal volume space as well as device contents. Exemplary mesh materials are prepared with wood, wood composites, metal, metal composites, nonmental composites, plastics, fibers, and combinations thereof. Preferred materials include metals with good abrasion resistance. Mesh wire sizes and openings can be adjusted to the particle size, density, and moisture content of wastes, feedstocks and final products produced by devices of the invention. Experts in the field will understand the appropriateness of different materials and mesh openings to facilitate continuous, semi-continuous, and batch processing using devices.

The internal volume space of devices of the invention can be subdivided into zones, regions, partitions, or compartments. Subdivision of the internal volume space can be accomplished by using thin polymer films alone or in combination with rigid or semi-rigid internal structural supports. Preferred materials for subdividing the internal volume space are porous or contain apertures, holes, slits, or a combination thereof, and allow control of organism movement throughout the subdivisions. Subdividing the internal volume space is useful for separating feedstocks with varying carbon to nitrogen ratios, wastes and feedstocks in varying stages of composting, separating different organisms, and separating organisms in different stages of their lifecycle.

Exemplary organism separations include the separation of mature worms from cocoons, and the separation of fly larvae from flies. Subdivision of the volume space is also useful for providing device structural support and assisting in maintaining device shape. Preferred subdivision of the internal volume space includes corners of devices. Exemplary materials for subdividing the internal volume space include similar polymer films as those used to prepare the external walls of the device as well as rigid materials including pvc, acrylics, polystyrenes, low and high density polyethylenes, polycarbonates, and similar materials.

Exemplary devices of the invention can be supported, positioned, transported, and manipulated using support structures attached to outside surfaces. External support structures can be prepared with rigid or semi-rigid materials, and utilize solid materials or open frame structures and can function in tandem with internal support structures. External support structures can take advantage of handles, loops, straps, and sleeves attached to the outside surface of devices.

Figure 5:
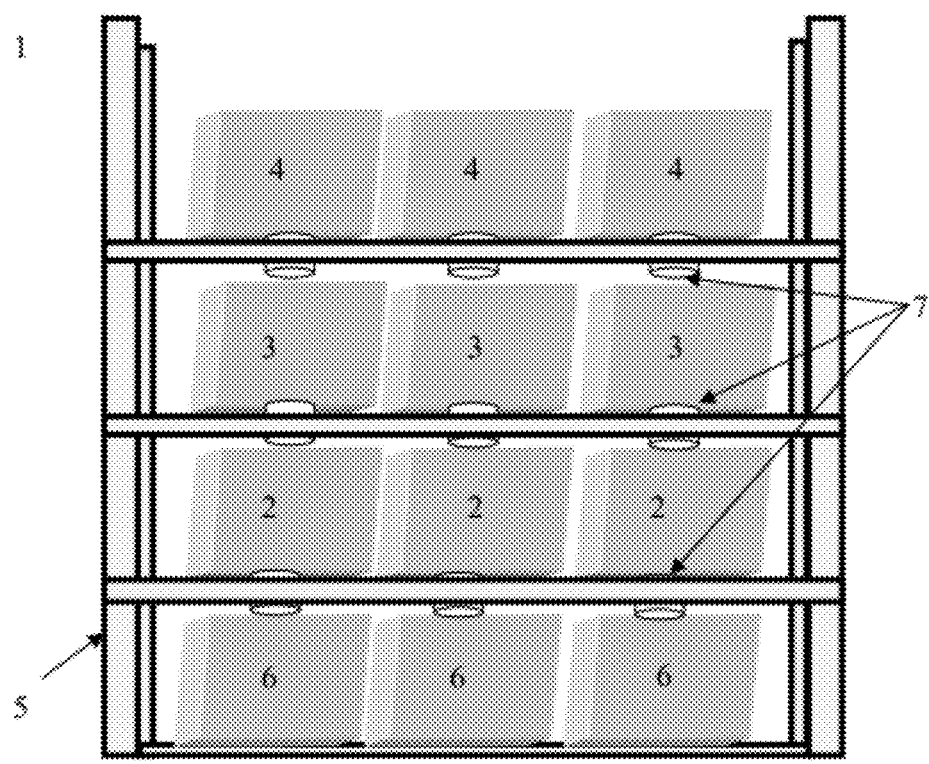
FIG. 5, a front view, illustrates one embodiment of the invention, a four-tier storage arrangement for devices as described in FIG. 2, wherein the top three tiers of devices can discharge their contents into devices positioned below.

Exemplary external support structures can be prepared with metal, wood, plastic, and composites thereof. The use of external support structures can also include industrial shelving and storage platforms commonly used for shipping containers and pallet storage. FIG. 5 provides an illustration of a shelving unit with an organized grouping of devices of the invention. Vertical organization allows the contents of higher positioned devices to be discharged into a lower positioned device. External support structures in combination with handles, sleeves, and loops attached to devices of the invention allow inversion and rotation of devices in three-dimensions, aiding in mixing of device contents and improving material transformation and handling.

Devices of the invention can be completely enclosed using reversible tight seals. Devices are sealed reversibly using pressure clips, fasteners, and ties that compress the thin polymer films used to prepare devices. Exemplary locations for tight reversible seals include the top of devices that comprise an integrated lid and the bottom of devices. Preferred locations for reversibly tight seals include material feed and discharge chutes, ports, and spouts.

Reversible tight seals allow devices to be repeatedly opened for loading wastes, feedstocks, organisms, and adjuvants, and discharging finished products and organisms. Enclosing devices after these operations allows the environmental conditions of the internal volume space of devices to be manipulated and controlled. Tight seals allow organisms and feedstocks to remain inside devices when shipped, rotated, or positioned. Tight sealing of devices of the invention is possible when containing living organisms and completing composting, vermicomposting, and vermiculture operations, all of which need oxygen for respiration, because the thin polymer films of the invention are breathable and allow efficient gas exchange. Reversible seals for feed and discharge elements also allow lighting and temperature to be controlled more precisely. Exemplary mechanisms include ties, ropes, plastic and metal clips, spring containing clips, metal tension rings, magnetic clips, and combinations thereof. Automated closing mechanisms can also be used.

Devices of the invention can comprise molded components internally, externally, or a combination thereof, to provide ports, and mounting assemblies for conduits and piping used to provide access to the internal volume space of sealed devices, sensors and monitoring equipment, and process equipment, and connections between devices. Molded devices may be used to provide repetitive access through the thin polymer films into internal volume spaces. Exemplary materials for preparing ports and conduits include phenolic resins, polypropylene, LD polyethylene, MD polyethylene, HD polyethylene, polyvinyl chloride, polyethylene terephthalate, glycol modified polyethylene terephthalate, polycarbonate, cyclo-olefin copolymer, nylon 6, polyethylene naphthalate, and polystyrene. Those expert in the field will understand the chemical and physical properties of these materials, their suitability for vermiculture, vermicomposting, and composting, and optimum positions. Preferred locations are in device side walls which leaves lids and floors clear, facilitating the loading and unloading of devices.

Devices of the invention can include printed elements that provide significant utility to device operators. Printing in the form of writing, pictures, textured elements, or a combination thereof can be applied directly to the thin polymer films or indirectly through the printing of labels and subsequent adhesion of the labels to the thin polymer films Printing can affect device function by controlling light, moisture, breathability, and temperature. A device's external surface can support general marketing and product identification text as well as instructions for device use. Instructions can be in the form of text, pictures, diagrams, and combinations thereof. Further, simple printed markings allow device operators to accurately and precisely monitor loading and unloading volumes, and masses of device contents. This information simplifies daily operations.

Printing technology can also quickly relay important culture and composting system information to operators, including temperature, lighting levels, and chemical concentrations. Exemplary indicator systems can be created with printing and coating technology that utilizes thermochromics, which provide temperature information through color changes, photochromics which provide lighting and illumination information through color change, and chemochromics, which provide chemical information through color change. Exemplary thermochromic technology utilizes liquid crystals, leucodyes, and combinations thereof. Exemplary photochromic and chemochromic technologies use organic and inorganic compounds including dyes, pigments, carriers, and combinations thereof. Those experienced in the field will further understand the film characteristics required for direct printing on film surfaces as well as the use of adhesives when applying labels to film surfaces. Common print methods include gravure, inkjet, and flexographic techniques.

Worms, insect larvae, insects, bacteria, fungi, molds, acetinomycetes, nematodes, protozoa, rotifers, springtails, mites, beetles, and a wide range of other microorganisms and invertebrates are present in composting materials and form complex food webs and communities. Those expert in the field understand that there are thousands of species that may participate in waste and feedstock breakdown and mineralization and that their presence and dominance in composting feedstocks will vary with different feedstocks and environmental conditions.

It is estimated that there are more than 4000 species of terrestrial worms. The identification, culture, and general understanding of these organisms is difficult and in many cases limited. More common earthworms are represented by the families Lumbricidae, Eudrilidae, Microchaetidae, Megascolecidae, and Glossocscolecidae. Earthworms can be further categorized as endogeic, anecic, and epigeic, which are commonly defined as soil feeders, burrowers, and surface feeders. Earthworms associated with these classifications are suitable for incorporation and manipulation in devices of the invention.

Preferred worm species include *Eisenia andrei, Eisenia fetida, Dendrodrilus rubidus, Dendrobaena veneta, Lumbricus rubellus, Drawida nepalensis, Eudrilus eugeniae, Perionyx excavatus*, and *Polypheretima elongata*. It should be recognized that many earthworm species have common names. As example, *Eisenia andrei* and *Eisenia fetida* are referred to as redworms, striped worms, brandling worms, and tiger worms.

It is well recognized that different species of worms have different vermiculture, vermicomposting, and environmental requirements including bedding materials, feedstocks, moisture, lighting, and temperature. In addition, experts in the field will understand conditions suitable and optimal for procreation, propagation, cocoon production, cocoon hatching and the efficiencies of each process with respect to temperature, moisture, feedstock, lighting, and density of the same, similar, and different species.

Preferred insect larvae and insects include the Black Soldier Fly (BSF), *Hermetia illucens*, classified in the family, Stratiomyidae, fruit flies classified in the family Drosophilidae, and house flies classified in the family, Muscidae.

New species of worms, insects, bacteria, fungi as well as other compost relevant organisms are the focus of study and are undergoing identification and classification. These new species are anticipated to be appropriate for inclusion into devices of the invention.

Organic and inorganic wastes and feedstocks suitable for vermiculture, vermicomposting, and composting have been studied and are generally well known. Exemplary wastes and feedstocks suitable for vermiculture, vermicomposting, and composting include all types of animal wastes, agriculture, horticulture, and landscape wastes, municipal wastes that contain food scraps, paper, and biodegradable materials, and industrial wastes that contain cellulose and other natural polymers.

In practice, different types of waste materials are mixed together to provide optimum carbon to nitrogen ratios, moisture, and oxygen penetration to maximize the rate of microbial decomposition. Optimum mixing ratios, temperatures, moisture contents, and oxygen take-up rates have been well researched and published. It is generally understood that microorganism based composting proceeds through mesophyllic and thermophyllic stages, and the duration and efficiency of these stages depends upon both the composition of the waste materials, and the chemical, biological, and physical parameters associated with the composting technique.

Worms and insect larvae are well understood to prefer lower temperatures than those present in mesophyllic and thermophyllic composting stages. As a result, it is common practice to compost certain feedstocks and wastes before introducing them to earthworms and insects. Additionally, preparation of feedstocks for vermiculture and vermicomposting often include particle size reduction, moisture adjustment, and tailoring of microorganism populations. It is well recognized that worms and insect larvae ingest microorganisms along with organic wastes and feedstocks and can receive nutrition from these microorganisms. It is also understood that earthworms and insect larvae often work synergistically with microorganisms to transform wastes into composts, vermicomposts, and castings.

When pathogens, weed seeds, and undesirable chemical agents might be present in wastes and feedstocks pretreatment can reduce and eliminate these components before earthworms are employed to transform the materials. In many cases, environmental regulations require that all waste and feedstocks are treated at elevated temperature prior to use by the public. An exemplary regulatory threshold is described in 40 CFR Part 503, as amended Jul. 1, 2002. In practice, feedstocks meet regulations when exposed to a thermophyllic stage of at least 55° C. for at least 72 hours. During this treatment stage and the following mesophyllic stage, pathogenic organisms that may have been originally present are destroyed by temperature and "out-competed" by non-pathogenic microorganism growth. In some cases, wastes with high nitrogen contents undergo more than one composting cycle where each cycle includes a thermophyllic and mesophyllic stage. It is common for these preparative composting steps to require more than two days for each stage of the cycle.

Organic and inorganic wastes and feedstocks often require chemical parameters to be adjusted to optimize composting and vermicomposting transformation rates and to maximize their suitability as feedstocks for vermiculture and insect culture. Chemical tolerances of worms to pH, salinity, and ammonia as well as other chemicals have been published. Important parameters also include carbon to nitrogen ratios, pH, buffer capacity, and moisture content. In some cases, additives are used to increase microorganism populations and their metabolic activity. Additionally, adjuvants that reduce toxicity to animals are utilized and include chemicals which bind and detoxify heavy metals, pesticides, and anti-microbial agents. Reagents and adjuvants suitable for use are available as solid and liquids. In most cases, liquid preparations are preferred. Exemplary reagents and adjuvants are used to neutralize ammonia, reduce oxidants such as chlorine, bromine, and oxygen containing compounds, and to bind or chelate heavy metals.

Exemplary reagents and adjuvants that can be used to increase microorganism populations and metabolism contain carbon, nitrogen, phosphorus, potassium, trace elements, metals and vitamins as well as simple sugars and carbohydrates. Experts in the field understand that many reagents and adjuvants exist and that they can be included in operations when transforming waste materials and feedstocks with devices of the invention.

Metabolic byproducts of worms and insects including vermicomposts and castings, are well known to be highly beneficial as organic fertilizers, seed starting mediums, and have been demonstrated to carry plant growth stimulants and protective agents. Use of these materials as well as solid and liquid preparations of these materials are widely discussed and publicized in agriculture, horticulture, landscaping, and gardening forums. New methods, regulations, and protocols are anticipated to be identified or required for wastes and feedstocks processed by composting, vermicomposting, and for supporting vermiculture and insect culture and that devices of the invention will be suitable for successfully completing these methods.

Devices of the invention can function efficiently in both indoor and outdoor locations, and are unique in their portability which facilitates transport between locations. Devices of the invention utilize high strength, thin polymer films which are breathable, but will not hold bulk water. However, both woven and nonwoven thin polymer films used in devices of the invention will block precipitation from entering devices. This allows devices containing integrated lids or tops to block precipitation while allowing excellent gas exchange between the internal volume space and the surrounding atmosphere. These films also provide temperature control when used outdoors. Dark colored films assist in retaining heat, while light colored films help reflect sunlight. Opaque films are preferred as worms and insect larvae are sensitive to light.

External lighting can be used efficiently with devices of the invention. Proper choice of lighting in combination with woven polymer films allows enough light to enter sealed devices to assist in retaining organisms. Exemplary lighting includes fluorescent, halogen, LED, incandescent, and metal vapor. Preferred films and lighting include woven polypropylene and white LEDs. Experts in the field will understand the advantages and disadvantages of light sources including thermal and energy efficiency characteristics, and understand the optimum frequency and intensities for devices of the invention.

Wastes, feedstocks, and organisms can be loaded into devices, mixed and discharged from devices through a range of different operations and using automated or manual equipment. Exemplary equipment includes conveyors, hoppers, buckets, shovels, hoses, and the like. This equipment is readily available at most container loading, unloading, and shipping facilities, as well as warehouses, food production facilities, and agriculture operations. Wastes and feedstocks may be rapidly loaded into devices in sequential layers or in homogeneous bulk. Organisms may be introduced into devices together with feedstocks or separately. Devices of the invention can also rapidly discharge contents into processing equipment that provides mixing, screening, sorting, size reduction, and separation of components including organisms, metabolic byproducts such as finished composts, vermicomposts, and castings, as well as wastes and feedstocks that require further processing. During this processing, materials can be further modified to prepare finished products and reloaded into devices for storage, transport, or a combination thereof. Common waste and feedstock modifications include organism inoculation, and adjustment of material chemical and physical parameters.

Mixing of device contents may also be completed through rotation of devices in three dimensions utilizing external supports, handles, sleeves, straps, and loop structures integrated into devices or temporarily attached to the outside of devices. It is well known in the field of vermiculture, vermicomposting, and composting that bulk materials prepared in large volumes undergo compression and volume reduction which can impede waste and feedstock transformation, access to waste and feedstock by organisms, as well as discharge of device contents. Compression and compaction can also lead to inhomogeneities in oxygen, moisture, and temperature levels and impede modification of these parameters. Rotation and manipulation including shaking and vibrating can be used to mix, aerate, and modify the homogeneity and compaction characteristics of device contents. These manipulations are important in batch processing. Experts in the field will understand the limitations associated with material particle size, moisture content, density, and suitability with respect to mixing efficiency and device structural characteristics, and the impact that these parameters and operations have on organisms present in devices.

DETAILED DESCRIPTION OF FIGURES

FIG. 1.

FIG. 1 illustrates one embodiment of the invention, a view of the front face of a rectangular device made from opaque, flexible, and breathable, woven polypropylene polymer thin films which are sewn around their periphery, (1); that defines a single internal volume space (10). The device comprises an integrated floor (2), which may be planar (as shown), tapered, or conical, and which comprises an integrated material discharge chute (6), with integrated resealable ties (7). The resealable discharge chute may also be, optionally, fitted with automated opening, closing, and pressure plate assemblies to allow continuous release of finished products. The device also comprises an optional integrated lid (3), with integrated resealable ties (8); and four loop style handles, (9), for elevation and transport. The device's internal volume space contains worms in a feedstock comprising organic and inorganic materials (4), and finished castings and vermicompost below the worms and feedstocks, (5). When devices comprise an integrated lid, this lid may contain an optional material input chute, funnel, or aperture which is resealable.

FIG. 2.

Figure 2:
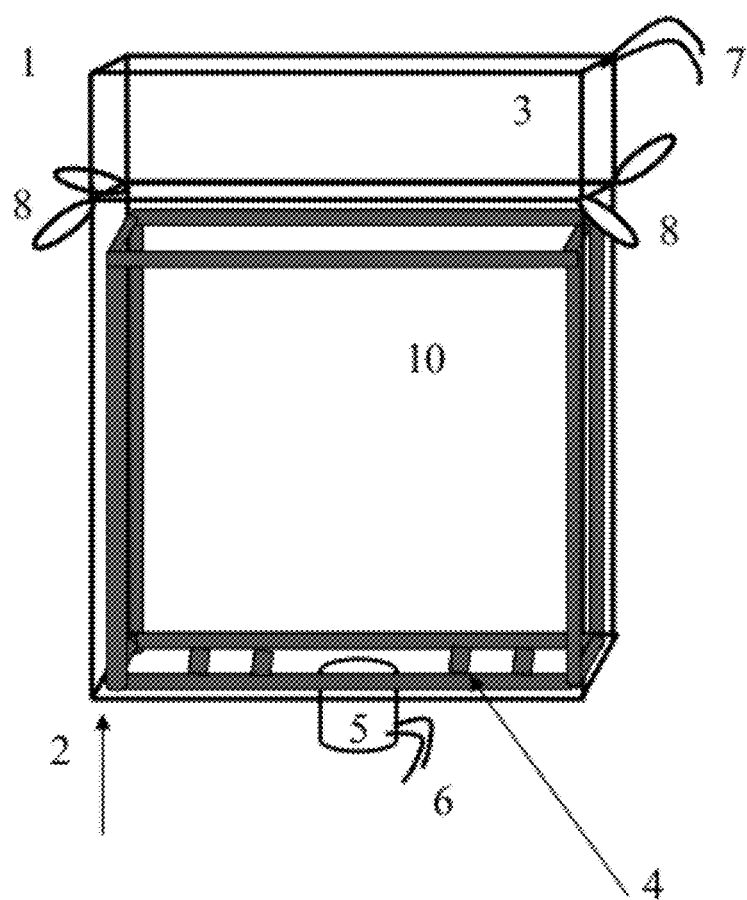
FIG. 2, a front view, illustrates one embodiment of the invention, a rectangular device made from high strength, woven, flexible, and breathable thin polymer films, comprising a single internal volume space, an integrated resealable lid, discharge chute, handles for elevation and transport, and an internal support structure.

FIG. 2 illustrates one embodiment of the invention, a view of the front face of a rectangular device made from opaque, flexible, and breathable, woven polypropylene polymer thin films which are sewn around their periphery, (1); that defines a single internal volume space (10). The device also comprises an optional integrated lid (3), with integrated resealable ties (7); and four loop style handles, (8), for elevation and transport. Four additional handles may be placed at the bottom four corners of the device (not shown). The device also comprises an internal rigid hollow and perforated pvc support structure, (4). The internal support structure is integrated with the thin polymer films by sewing. The device comprises an integrated floor (2), which may be planar (as shown), tapered, or conical, and can be formed with the thin polymer films entirely or supported in conjunction with the internal support; and which comprises an integrated material discharge chute (5), with integrated resealable ties (6). The device's internal volume space contains worms in a feedstock comprising organic and inorganic materials, and finished castings and vermicompost below the worms and feedstocks. The device contents are not shown for diagram clarity. When devices comprise an integrated lid, this lid may contain an optional material input chute, funnel, or aperture which is resealable.

FIG. 3.

Figure 3:
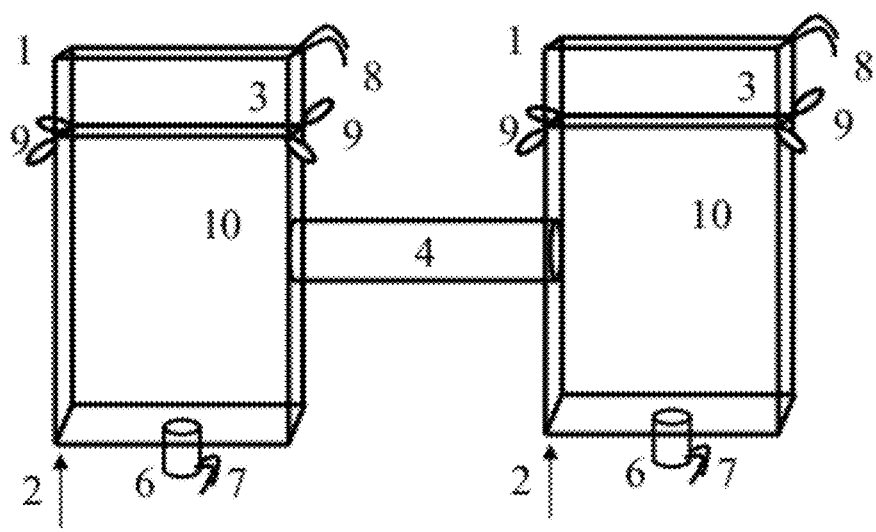
FIG. 3, a front view, illustrates one embodiment of the invention, two rectangular devices made from high strength woven, flexible and breathable thin polymer films, each comprising a single internal volume space, integrated resealable lid, discharge chute, and handles for elevation and transport. Devices are connected by a common conduit.

FIG. 3 illustrates one embodiment of the invention, a view of the front face of two rectangular devices made from opaque, flexible, and breathable, woven polypropylene polymer thin films which are sewn around their periphery, (1); that defines a single internal volume space (10). Each device comprises an integrated floor (2), which may be planar (as shown), tapered, or conical, and which comprises an integrated material discharge chute (6), with integrated resealable ties (7). Each device also comprises an optional integrated lid (3), with integrated resealable ties (8); and four loop style handles, (9), for elevation and transport. The devices are connected with a conduit (4). One device's internal volume space can contain worms in a feedstock comprising organic and inorganic materials and finished castings and vermicompost, while the other device can contain only feedstocks. Device contents are not shown for clarity. When devices comprise an integrated lid, this lid may contain an optional material input chute, funnel, or aperture which is resealable. These devices may additionally, contain an integrated support structure.

FIG. 4.

Figure 4:
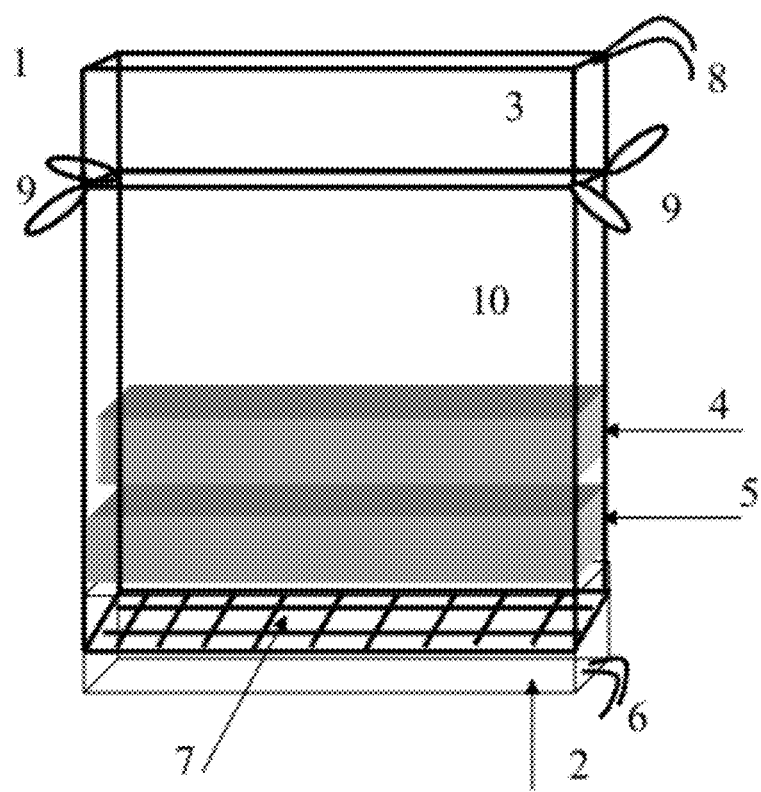
FIG. 4, a front view, illustrates one embodiment of the invention, a rectangular device made from high strength woven, flexible, and breathable thin polymer films, incorporating a single internal volume space, integrated mesh floor, integrated resealable lid and floor, and handles for elevation and transport.

FIG. 4 illustrates one embodiment of the invention, a view of the front face of a rectangular device made from opaque, flexible, and breathable, woven polypropylene polymer thin films which are sewn around their periphery, (1); that defines a single internal volume space (10). The device comprises an integrated floor (2), which may be planar (as shown), tapered, or conical, and that comprises integrated resealable ties (6). The device also comprises an optional integrated lid (3), with integrated resealable ties (8); and four loop style handles, (9), for elevation and transport. Above the device floor is an integrated rigid metal mesh floor, (7) which is integrated with the thin polymer films through sewing. The mesh floor provides structural and device content support as well as continuous removal of finished products. The device's internal volume space contains worms in a feedstock comprising organic and inorganic materials (4), and finished castings and vermicompost below the worms and feedstocks, (5). When devices comprise an integrated lid, this lid may contain an optional material input chute, funnel, or aperture which is resealable.

FIG. 5.

FIG. 5 illustrates one embodiment of the invention, a view of the front face of a series of twelve devices, (1); arranged in four rows, the device series (4,3,2,6) are stacked on industrial quality shelving, (5). Device series (4,3,2,6), are positioned in close proximity to each other to control temperature but not limit air-flow. Device series (4,3,2) comprise floors with integrated discharge chutes, (7), that serve as feeds for devices positioned below. Exemplary devices that can be organized in this manner are described in FIG. 2.

BENEFICIAL CHARACTERISTICS OF THE INVENTION

Devices and methods of the invention greatly expand the locations and opportunities where composting, vermicomposting, and vermiculture can be employed for processing and transforming wastes and feedstocks. Most organic and inorganic waste streams and feedstocks are dynamic, frequently varying in material types, volumes, and moisture contents. Modular and portable devices of the invention can efficiently handle more than one hundred pounds of waste materials per day. This waste capacity allows the tremendous number of medium size waste streams now present with retail food and beverage services to be addressed. In all cases, devices of the invention allow organic waste streams to be managed and efficiently transformed into beneficial soil, agriculture, and gardening products.

Light-weight and portable devices of the invention eliminate the need for installing large, permanent, and heavy structures that are currently standard practice. Larger volume waste streams are handled simply by increasing the number of devices at the waste site. This modular approach reduces capital costs of projects and efficiently uses site space.

Devices of the invention allow tremendous flexibility in performing composting, vermicomposting, and vermiculture operations. Devices of the invention can be operated directly on the ground, elevated above ground supported using simple ground based supports, or elevated above ground using simple hoists. Locating devices above ground allows continuous flow-through operations.

Devices of the invention allow easy movement, positioning, rotation, and transport using commercially available equipment. Throughout all operations, devices of the invention allow internal volume space to be maintained. Equally important, devices of the invention allow device location and type of support to be rapidly changed in order to better address waste stream characteristics and to improve the rate of waste transformation.

Devices of the invention are very flexible allowing operations to vary based on location, type of waste stream, and availability of manual or automated equipment. Devices may be operated with open tops as is typical of current large scale flow through vermicomposting operations or with closed tops using integrated lids and appropriate sealing mechanisms including ties, and fasteners. Fully enclosed devices allow greater control of environmental parameters, regulations requiring elevated temperature treatments to be met, and provide a simple low energy method of confining worms, insects, and other beneficial organisms.

Devices of the invention allow quick loading and unloading of wastes, feedstocks, finished products such as composts, vermicomposts, and castings, and animals. Rapid loading is typically completed through a device's open top, funnel, spout, or chute. Rapid discharge of device contents is typically through a bottom mesh screen, chute, spout, or full opening of the device bottom. The presence of a thin film floor allows initial startup of operations to forgo the use of cardboard and other bed or barrier materials used to retain wastes and feedstocks in devices with permanently open bottoms.

Rapid discharge of device contents allows frequent use of mixers, screens, and aeration devices, which collect, separate, and condition materials for use as final products or for return to devices for further transformation. These final or intermediate processing steps provides greater control of waste and feedstock transformation rates through better control of environmental parameters and transformation conditions, including particle size, moisture content, temperature, aeration, and chemical element ratios. This capability is also very useful for the rapid collection and separation of animals from starting and finished materials. Additionally, this operational flexibility allows all modes of composting, vermicomposting, and vermiculture, including batch, semi-continuous, and continuous modes, to be conducted cost-effectively in the same device. This capability is not present in current large scale continuous flow systems.

Devices of the invention provide a superior ability to safeguard and control the spread of disease or contamination in composting, vermicomposting, and vermiculture systems, by using modular enclosed systems. The use of modules allows specific problem modules to be isolated and quarantined in order to reduce and eliminate the spread of the problem, and keep waste stream management and transformation on-line. The isolation of modules also allows organisms which are not compatible to participate in waste stream and feedstock transformation in close proximity. The modular design of devices of the invention allows controlled studies of soils to be conducted and the evaluation of agricultural products to be tested in a cost effective manner.

Devices of the invention comprise low-cost materials that are available globally. Recycled materials can be used for the preparation of devices, further lowering costs and reducing a waste stream, and after the device lifetime has been reached, recycled again. Devices require very little maintenance for use, there are no moving parts or energy sources required to operate. Devices of the invention can be setup and placed into operation faster than any known device of its scale. Devices of the invention allow seasonal, dynamic, and temporary waste streams of significant size to be managed and resolved without the construction of large, permanent or heavy traditional structures.

Devices of the invention that are fully active and operational for vermiculture and vermicomposting can be efficiently transported using standard commercial road, train, barge, ship, and air methods. Devices of the operation are also immediately suitable for use as a storage container for finished products including composts, vermicomposts, castings, and animals including worms, and insects and their larvae. Devices conform to standard shipping sizes and regulations.

Devices of the operation are also immediately suitable for use as preparation containers for generating and formulating teas, extracts, and solutions, from finished composts, vermicomposts, and castings. Liquid preparations can be prepared by directly adding water and other aqueous solutions into a device's internal volume space. The inability of the devices to hold bulk water allows the extracts, teas, and liquid formulation to drain out of devices. As a result, devices of the invention can be used at every step of transforming wastes and feedstocks into finished products that are beneficial for use in agriculture, horticulture, landscaping, and gardening.

Low start-up costs, rapid operation start-up indoors or outdoors, and the light-weight portable nature of devices allows more types of waste streams and feedstocks to be addressed with vermicomposting, composting, and vermiculture technologies and a reduction in business risk associated with waste management activities. As a result, devices of the invention allow greater amounts of waste to be recycled and reused, avoiding the dumping in landfills where much of this material is lost to greenhouse gas generation. It also allows the recovery of valuable plant nutrients that are at best sequestered in landfills and at worst leached into waterways.

SPECIFIC USE AND PREFERRED EMBODIMENTS

Exemplary and preferred embodiments of the invention are described in the following Examples. These Examples while illustrative are not meant to be fully descriptive of the utility and functionality of devices and methods of the invention. Devices can be scaled and sized to meet the requirements of many different specific waste stream and feedstock applications. Those experienced in the relevant art associated with each of these Examples will understand the size of devices and parameters required to successfully address vermiculture, composting, and vermicomposting applications. Likewise, those experienced in the relevant art will understand the many applications and beneficial uses of worms, castings, compost, and vermicompost.

EXAMPLES

Example 1

A ten-pound mixture of redworms including the species *Eisenia fetida* were placed inside a device similar to that illustrated in FIG. 2. The device was approximately 35 inches (long)×35 inches (wide)×28 inches (deep) and comprised an integrated lid with a duffel-drawstring tie and a planar bottom with a duffle-spout-tie system. The device was prepared from woven breathable polypropylene film with a carrying strength of approximately 4000 pounds and an internal support structure prepared with perforated one-inch plastic pipe. The support structure was sewn to the woven polypropylene film. The device was supported approximately four feet above ground using chains and loop-style handles attached to the outside surface of the device.

Over a six-month period the device was subject to external temperatures between 55° F. and 90° F. The bed temperature inside the bag varied spatially between 65° F. and 110° F. as a result of regions of mesophyllic bacteria activity. Regions that exceeded 90° F. contained few worms as they migrated to regions of lower temperature. When all regions of the internal volume space were below 90° F. worms were consistently spread uniformly.

Worms were fed frequently each week with macerated kitchen wastes including coffee grounds, fruit, and vegetable waste. Feedstock also included moistened cardboard and paperstock that had been shredded. The device was operated in a flow-through manner with worms continually metabolizing feedstocks and producing stable high quality castings. Worms were observed to move up into each successive new layer of feedstock, leaving castings and vermicompost below them. No leachate was generated.

It has been observed that worms crawl on all interior surfaces during the day and night, and throughout the full volume of feedstocks and wastes placed in the device. The worm bed supported a wide range of small insects and their larvae including fruit flies, and soldier flies. Worms were also seen in pairs and groupings on all surfaces including the integrated lid. Worm cocoons were frequently found throughout the castings and immature worms were routinely observed. Without wishing to be bound by a single theory, the enclosure provides a humid environment with static air, that is similar to the leaf litter and composting biomass piles that these organisms are naturally found.

Example 2

A ten-pound mixture of redworms including the species *Eisenia fetida* were placed inside a device similar to that illustrated in FIG. 2. The device was approximately 35 inches (long)×35 inches (wide)×28 inches (deep) and comprised an integrated lid with a duffel-drawstring tie and a planar bottom with a duffle-spout-tie system. The device was prepared from woven breathable polypropylene film with a carrying strength of approximately 4000 pounds and an internal support structure prepared with perforated one-inch plastic pipe. The support structure was sewn to the woven polypropylene film. The device was supported approximately four feet above ground using chains and loop-style handles attached to the outside of the device.

Worms were fed with composted organic waste that included coffee grounds, fruit, and vegetable waste, shredded cardboard and paper stock, leaves, and landscaping wastes. Compost was prepared in a device similar to that which housed the worms, and included a 72 hour treatment stage with temperatures above 150° F.

The device was operated in a flow-through manner with worms continually metabolizing feedstocks and producing stable high quality castings. No leachate was generated. Worms were observed to move up into each successive new layer of feedstock, leaving castings and vermicompost below them. The worm bed supported a wide range of small insects and their larvae including fruit flies, and soldier flies. Worms were observed to move throughout the device on all surfaces during both day and night time periods. Worms were also seen in pairs and groupings on all surfaces including the integrated lid. Worm cocoons were frequently found throughout the castings and immature worms were routinely observed.

Example 3

Composted organic feedstocks were prepared inside a device similar to that illustrated in FIG. 2. The device was approximately 35 inches (long)×35 inches (wide)×28 inches (deep) and contained an integrated lid with a duffel-drawstring tie and a planar bottom with a duffle-spout-tie system which was centered. The device was prepared from woven breathable polypropylene film and has a carrying strength of approximately 4000 pounds. The device comprised an internal support structure prepared with perforated one-inch plastic pipe that was sewn into the device.

Over a six-month period the device was used in an environment with external temperatures between 55° F. and 90° F. Approximately, 1000-1500 pounds of compost was prepared using kitchen, fruit, and vegetable waste mixed with shredded cardboard. Moisture was added as needed, and the bag contents periodically aerated through mixing to maintain internal temperatures above 100° F. Compost preparation included a 72 hour period with temperatures above 150° F. No leachate was generated.

Example 4

Composted organic feedstocks were prepared inside a device similar to that illustrated in FIG. 2. The device was approximately 35 inches (long)×35 inches (wide)×28 inches (deep) and contained an integrated lid with a duffel-drawstring tie and a planar bottom with a duffle-spout-tie system which was centered. The device was prepared from woven breathable polypropylene film and has a carrying strength of approximately 4000 pounds. The device comprised an internal support structure prepared with perforated one-inch plastic pipe that was sewn into the device.

Over a six-month period the device was used in an environment with external temperatures between 55° F. and 90° F. Approximately, 1000-1500 pounds of compost was prepared using shredded leaves collected from residential yards mixed with alfalfa. Moisture was added as needed, and the bag contents periodically aerated through mixing to maintain internal temperatures above 100° F. Compost preparation included a 72 hour period with temperatures above 150° F. No leachate was generated.

The invention claimed is:

1. A vermiculture device for living organisms comprising one or more flexible, gas permeable polymer films sealed along an edge to define an interior volume space, an external support structure, and an internal support structure that allows the one or more flexible, gas permeable polymer films to maintain a permanent shape and define a fixed interior volume; wherein the internal support structure is secured to the one or more flexible, gas permeable polymer films by sewing, integrated weaving, thermal sealing, adhesives, use of dedicated sleeves, or a combination thereof; wherein the internal support structure allows for the exchange of gases between the interior and the exterior of the device; and wherein the exchange of gases occurs, at least in part, through the internal support structure.

2. The vermiculture device of claim 1 wherein the shape is square, rectangular, cylindrical, or barrel.

3. The vermiculture device of claim 1 comprising an integrated flexible polymer film lid, floor, or combination thereof.

4. The vermiculture device of claim 1 comprising an integrated flexible polymer film lid wherein the lid comprises a polymer film chute, spout, or funnel.

5. The vermiculture device of claim 1 comprising an integrated flexible polymer film lid, wherein the lid comprises sealing and resealing elements, wherein the sealing and resealing elements are duffle ties, clasps, or fasteners.

6. The vermiculture device of claim 1 comprising an integrated flexible polymer film floor wherein the floor comprises, a polymer film chute, spout, or funnel.

7. The vermiculture device of claim 1 comprising an integrated flexible polymer film floor, comprising sealing and resealing elements, wherein the sealing and resealing elements are duffle ties, clasps, or fasteners.

8. The vermiculture device of claim 1 wherein the flexible gas permeable polymer films comprise woven films, nonwoven films, coated films, laminated films, opaque films, transparent films, or combinations thereof.

9. The vermiculture device of claim 1, wherein the polymer film edges are sealed together by sewing, thermal sealing, adhesives or a combination thereof.

10. The vermiculture device of claim 1, wherein the internal support structure controls environmental conditions within the internal volume space, wherein the environmental conditions comprise, temperature, humidity, oxygen levels, moisture levels, or combinations thereof.

11. The vermiculture device of claim 1 further comprising printing elements, wherein the printing elements comprise marketing information, purchase information, culture instructions, disposal instructions, chemical concentration indicators, physical parameter indicators, temperature indicators, lighting indicators, organism density indicators, or a combination thereof.

12. The vermiculture device of claim 1, further comprising lifting hooks, loops, straps, or handles.

13. The vermiculture device of claim 1, further comprising an organism, wherein the organism is, bacteria, fungi, actinomycetes, invertebrates, protozoa, algae, yeast, mold, insect larvae, insects, ciliates, infusoria, nematodes, earthworms, worms, eggs, cocoons, cysts, or combinations thereof.

14. The vermiculture device of claim 1 wherein the internal volume space is separated into two or more compartments.

15. The vermiculture device of claim 1 comprising a component wherein the component is selected from the group consisting of conduit connections, valves, ports, caps, meshes, and combinations thereof.

16. The vermiculture device of claim 1, wherein the device is used for culturing living organisms.

17. The vermiculture device of claim 1, wherein the internal structural support subdivides the internal volume of space into subdivisions, thereby allowing control of movement of organisms through the subdivisions.

* * * * *